United States Patent
van Nuland et al.

(10) Patent No.: US 7,288,184 B2
(45) Date of Patent: Oct. 30, 2007

(54) PROCESS FOR MITIGATING ACIDS IN A SYSTEM FOR SEPARATING AROMATIC HYDROCARBONS FROM A HYDROCARBON FEEDSTREAM

(75) Inventors: Marcus Lambertus Hendricus van Nuland, Rijen (NL); John Joseph Monson, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 514 days.

(21) Appl. No.: 11/008,881

(22) Filed: Dec. 10, 2004

(65) Prior Publication Data

US 2006/0124509 A1 Jun. 15, 2006

(51) Int. Cl.
*C10G 17/04* (2006.01)
*C10G 21/28* (2006.01)
*C01F 1/00* (2006.01)
*B01D 11/00* (2006.01)

(52) U.S. Cl. .................... 208/311; 208/321; 423/111; 423/112; 423/120; 210/634

(58) Field of Classification Search ............. 208/311, 208/321; 423/111, 112, 120; 210/634
See application file for complete search history.

(56) References Cited

U.S. PATENT DOCUMENTS

| | | | |
|---|---|---|---|
| 2,878,182 A | 3/1959 | Bloch | 208/321 |
| 3,252,997 A | 5/1966 | Ridderikhoff et al. | 260/332.1 |
| 3,470,087 A | 9/1969 | Broughton | 208/321 |
| 3,492,222 A | 1/1970 | Van Tassell | 208/321 |
| 3,862,901 A * | 1/1975 | Wennerblom et al. | 210/665 |
| 3,864,245 A | 2/1975 | Van Tassell | 208/321 |
| 3,883,420 A | 5/1975 | Stone | 208/321 |
| 3,953,324 A | 4/1976 | Deal et al. | 208/321 |
| 3,985,648 A | 10/1976 | Casolo | 210/27 |
| 4,008,307 A * | 2/1977 | Loest et al. | 423/120 |
| 4,619,770 A | 10/1986 | Boston | 210/772 |
| 4,820,849 A | 4/1989 | Diaz et al. | 549/87 |
| 4,861,900 A | 8/1989 | Johnson | 549/87 |
| 4,919,816 A | 4/1990 | Tsao | 210/638 |
| 4,965,054 A * | 10/1990 | Lewis | 423/112 |

(Continued)

FOREIGN PATENT DOCUMENTS

| | | |
|---|---|---|
| CN | 1230545 | 10/1999 |
| CN | 1344716 | 4/2002 |
| EP | 0 380 879 | 3/1992 |
| EP | 0 551 002 | 4/1993 |
| EP | 0 979 811 | 2/2000 |

OTHER PUBLICATIONS

Abstract for CN 1230545 (see AS), published Oct. 6, 1999, entitled "Regeneration Process of Inferior Sulfolane—Using Anionic Exchange Resin Bed".

(Continued)

*Primary Examiner*—Melvin Mayes
*Assistant Examiner*—Huy-Tram Nguyen
(74) *Attorney, Agent, or Firm*—Michael Kerns

(57) ABSTRACT

Disclosed is a process for removing acids in a system in which aromatic hydrocarbons are separated from a mixture with aliphatic hydrocarbons. The aromatic hydrocarbons are extracted from the mixture using an extracting solvent. The aromatic hydrocarbons are stripped from the extracting solvent with steam and the steam is condensed to form water which is separated from the aromatic hydrocarbons. The separated water is passed through a basic anion exchange column and is then heated to produce the steam.

39 Claims, 2 Drawing Sheets

U.S. PATENT DOCUMENTS

| | | | | |
|---|---|---|---|---|
| 5,008,004 | A | * | 4/1991 | Maier et al. ................ 208/321 |
| 5,053,137 | A | | 10/1991 | Lal et al. .................... 210/669 |
| 5,059,306 | A | | 10/1991 | Krämer et al. ............. 208/313 |
| 5,225,072 | A | | 7/1993 | Vidueira ..................... 208/313 |
| 5,302,367 | A | * | 4/1994 | Signorini et al. ........... 423/588 |
| 5,518,628 | A | * | 5/1996 | Carey ......................... 210/686 |
| 5,879,540 | A | * | 3/1999 | Zinke et al. ................ 208/321 |
| 5,939,034 | A | * | 8/1999 | Virnig et al. ................ 423/24 |
| 6,123,850 | A | | 9/2000 | Commarieu et al. ........ 210/662 |
| 6,217,771 | B1 | * | 4/2001 | Boyle et al. ................ 210/638 |
| 6,375,802 | B1 | * | 4/2002 | Gentry et al. ............... 202/170 |

OTHER PUBLICATIONS

Abstract for CN 1344716 (see AT), published Apr. 17, 2002, entitled "Refining Process of Coarse Sulfolane Product".

Translation for EP 0 979 811 (see AV) by Ralph McElroy Translation Company, entitled "Method for Removing Organic and / or Inorganic Acids from Organic Phases", Feb. 16, 2000.

* cited by examiner

PROCESS FOR MITIGATING ACIDS IN A SYSTEM FOR SEPARATING AROMATIC HYDROCARBONS FROM A HYDROCARBON FEEDSTREAM

FIELD

This invention relates generally to a process for removing or mitigating acids in a system in which aromatic hydrocarbons are separated from a mixture with aliphatic hydrocarbons. In particular, it relates to extracting the aromatic hydrocarbons from the mixture utilizing a solvent, stripping the extracted aromatic hydrocarbons from the extracting solvent with a steam, condensing the steam, and processing the condensed steam through an anion exchange bed.

BACKGROUND

A common source of aromatics in petroleum refinery operations is catalytic reformed petroleum naphtha (reformate), which is prepared by contacting a mixture of petroleum naphtha and hydrogen with a strong hydrogenation/dehydrogenation catalyst, such as platinum, on a moderately acidic support, such as a halogen-treated alumina. Another source of aromatics is a catalytic cracking pyrolysis gasoline (pygas). Usually, a $C_6$ to $C_8$ fraction is separated from the reformate/pygas and extracted with a solvent selective for the aromatics or the aliphatics to produce a mixture of aromatic compounds that is relatively free of the aliphatics. Separation of the aromatic hydrocarbons from the aliphatic hydrocarbons may be accomplished by extracting the aromatic hydrocarbons using an extracting solvent such as tetraethylene glycol or sulfolane. The aliphatic hydrocarbons exit the extractor as raffinate. The raffinate is contacted with water in a wash column to remove dissolved solvent. The aromatic hydrocarbons are stripped from the extracting solvent with a steam. The steam is condensed. The condensed steam is separated from the aromatic hydrocarbons and sent to the raffinate wash column. This water is combined with water from the aliphatic hydrocarbon stripping tower overhead receiver. The combined water stream is sent to a water stripper where it is partially vaporized. To reduce pollution and maximize production, the water streams and extracting solvent streams are recycled. These two streams become acidic due to the accumulation of acids. This can cause corrosion and other process problems.

One solution to the problem of acidity is injection of small amount of a base (e.g., mono-ethanol amine (MEA)) to the extracting solvent. However, injection of the MEA can cause the formation of salts and/or polymers, which can cause the extraction unit solvent to foul. The fouled solvent can cause the unit to experience operational issues, for example, decreased hydrocarbon/solvent phase separation. This reduces the throughput of the extraction unit.

Another method of reducing acidity in this system is suggested in U.S. Pat. No. 4,919,816, where some or all of the water used to wash the aromatic product is passed through an anion exchange resin. Still another approach is disclosed in U.S. Pat. No. 2,878,182, where the extracting solvent is passed through an anion exchange column. Another method of reducing acidity is disclosed in U.S. Pat. No. 5,879,540, where the separated water is passed through a basic anion exchange column.

SUMMARY

In one embodiment, the invention relates to a process for producing hydrocarbons from a feed, comprising:
A) extracting from the feed at least a majority of aromatic hydrocarbons with a solvent to produce a first aromatic rich product and removing unextracted hydrocarbons as a second product;
B) separating at least a portion of the aromatic hydrocarbons from the solvent in the first product with steam;
C) condensing the steam to produce a first stream; and
D) processing at least a portion of the first stream through an anion exchange bed to produce a second stream.

In another embodiment, the invention relates to a process for removing acids in a system in which a feed including $C_4$ to $C_{12}$ hydrocarbons comprising:
A) extracting from the feed at least a majority of aromatic hydrocarbons with a solvent to produce a first product and removing unextracted hydrocarbons in the feed as a second product;
B) separating at least a portion of the aromatic hydrocarbons from the solvent in the first product with steam;
C) condensing the steam to produce a first stream;
D) washing the second product with the first stream; and
E) processing at least a portion of the first stream through an anion exchange bed to produce a second stream.

In another embodiment, the invention relates to a process for removing acids in a system in which a feed including $C_4$ to $C_{12}$ aliphatic and aromatic hydrocarbons comprising:
A) extracting from the feed at least a majority of aromatic hydrocarbons with a solvent to produce a first product and removing unextracted hydrocarbons in the feed as a second product;
B) separating the first product into an overhead product and a bottom product, condensing the overhead product to produce a condensed stream;
C) separating at least a portion of the aromatic hydrocarbons from the solvent in the first product with steam;
D) condensing the steam to produce a first stream;
E) washing the second product with the first stream;
F) combining the first stream from step (E) and the condensed stream from step (B);
G) processing at least a portion of the combined stream through an anion exchange bed to produce a second stream; and
H) heating the second stream to produce the steam in step (C).

In yet another embodiment of this invention, the process further comprises a switching means to switch the feed stream to the anion exchange bed from condensed steam to solvent.

BRIEF DESCRIPTION OF THE DRAWING

The FIG. 1 is a simplified process block diagram illustrating a preferred embodiment of this invention.

The FIG. 2 is a simplified process block diagram illustrating a preferred embodiment of a switching means of this invention.

DESCRIPTION OF THE PREFERRED EMBODIMENTS

Figure 1:
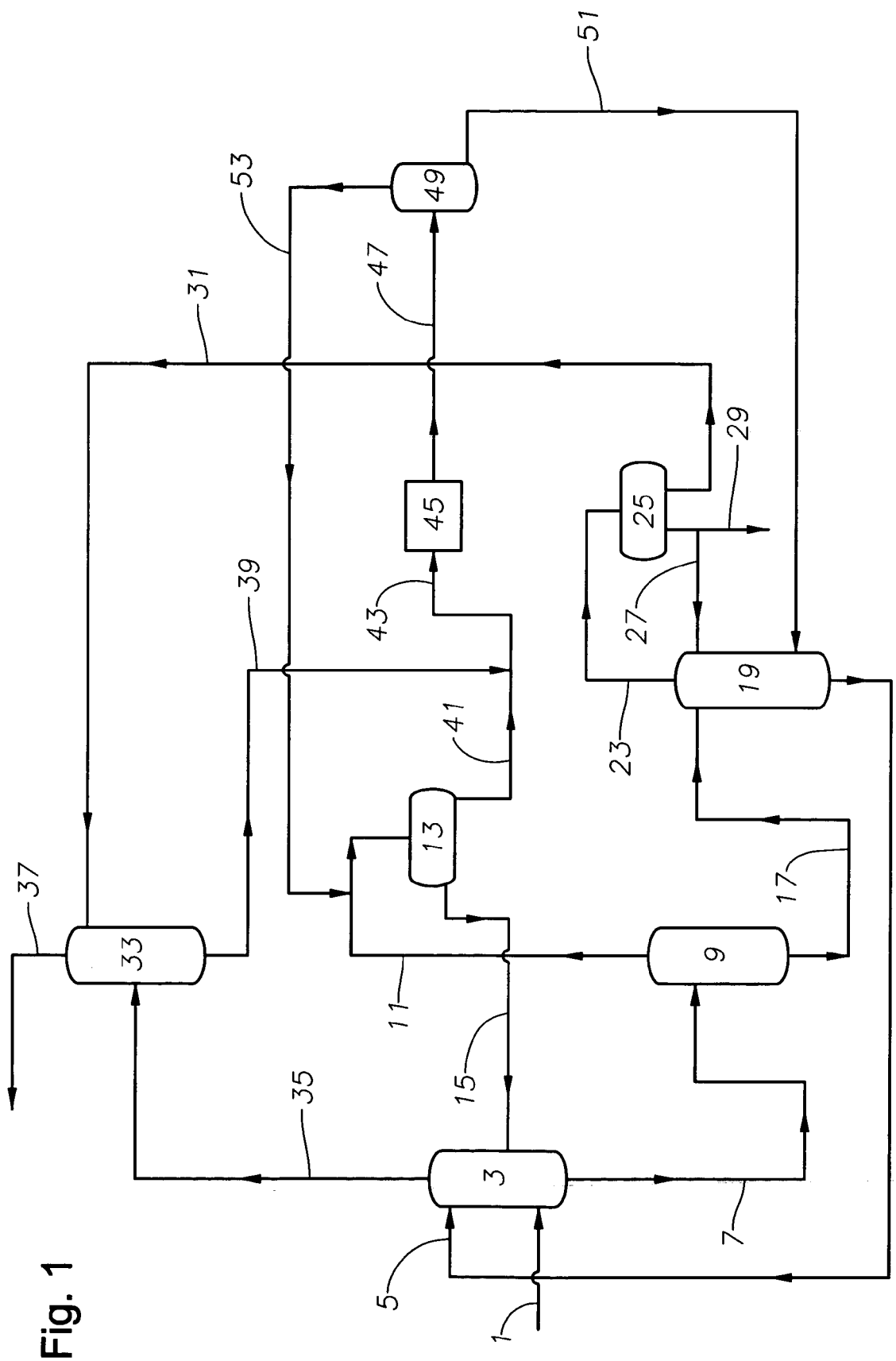

Referring to a preferred embodiment of this invention as illustrated in FIG. 1, a feed comprising $C_4$ to $C_{12}$ aliphatic and aromatic hydrocarbons is directed via line 1 to an extractor 3. Solvent is directed to the extractor 3 via a line 5. At least a portion of aromatic hydrocarbons in the feed is selectively dissolved in the solvent and withdrawn via a line 7 as a first product to a stripper 9 where a portion of nonaromatic components in the first product is removed by distillation as a stripper overhead. The stripper overhead comprising non-aromatics components, a small quantity of aromatics, solvent, and water is withdrawn via a line 11 and enters a stripper overhead receiver 13 to separate hydrocarbons from water. The hydrocarbons are then withdrawn from the stripper overhead receiver 13 via a line 15 and recycled to the extractor 3. Stripper bottom product from the stripper 9, substantially free of nonaromatic compounds, is sent via a line 17 to the recovery column 19, where the aromatic hydrocarbons product is separated from the solvent using a steam feed supplied via a steam supply line 51. The solvent from the recovery column 19 is recycled to the extractor 3 via the line 5. The aromatic hydrocarbons and water product of the recovery column 19 is directed via a line 23 to a recovery column overhead receiver 25 to separate water from the aromatic hydrocarbons product by condensing the steam to form a first stream comprising water, dissolving solvent and trace dissolving hydrocarbons, for example, hexane, benzene and toluene. A portion of aromatic hydrocarbons product is recycled to the recovery column 19 via a line 27 and the rest of aromatic hydrocarbons product is recovered as a extracted product via a line 29. The first stream is withdrawn from the recovery column overhead receiver 25 via a line 31 to raffinate wash tower 33 as a wash stream. The unextracted hydrocarbons in the feed of the extractor 3 are withdrawn from the extractor 3 as a second product comprising hydrocarbons, mainly non-aromatics, solvent, water, and dissolved aromatic hydrocarbons. The second product is withdrawn via a line 35 and directed to raffinate wash tower 33. In the raffinate wash tower 33, the second product is contacted with the wash stream from the recovery column overhead receiver 25 via the line 31 to remove dissolved solvent in the second product. The washed raffinate leaves raffinate wash tower 33 via a line 37 as a raffinate product. The washed stream comprising water, solvent, dissolved hydrocarbons, and contaminants, e.g., acids/acid salts, is withdrawn from raffinate wash tower 33 via a line 39 and combined with an aqueous stream from the stripper overhead receiver 13 via a line 41. The aqueous stream from the stripper overhead receiver 13 comprises water, solvent, dissolved hydrocarbons, and contaminants, e.g., acids/acid salts. The combined aqueous stream is directed via line 43 to an ion exchange bed 45 where substantially all contaminants (such as hydrochloric acid) are removed from the combined stream by ion exchange. In an alternative, only a portion of the combined stream is sent to the ion exchange bed 45 via line 43 and the rest of combined stream bypasses the ion exchange bed 45. The exchanged stream, now substantially free of contaminants, is further directed via a line 47 to a water stripper 49, where the water is vaporized to form steam. The steam is withdrawn from the water stripper 49 via a line 51 for use as the steam for the recovery column 19. The bottom product of the water stripper 49 is directed via a line 53 to the stripper overhead receiver 13 where hydrocarbons, solvent, and water are recovered.

In another embodiment of this invention, the ion exchange bed 45 is located in line 31. In yet another embodiment of this invention, the ion exchange bed 45 is located in the line of 31 and the exchanged stream from the anion exchange bed 45 feeds directly to the water stripper 49.

In another embodiment of this invention, the feed to the basic anion exchange bed 45 may be switched from the aqueous stream to the solvent separated in the recovery column 19 via line 5.

Figure 2:
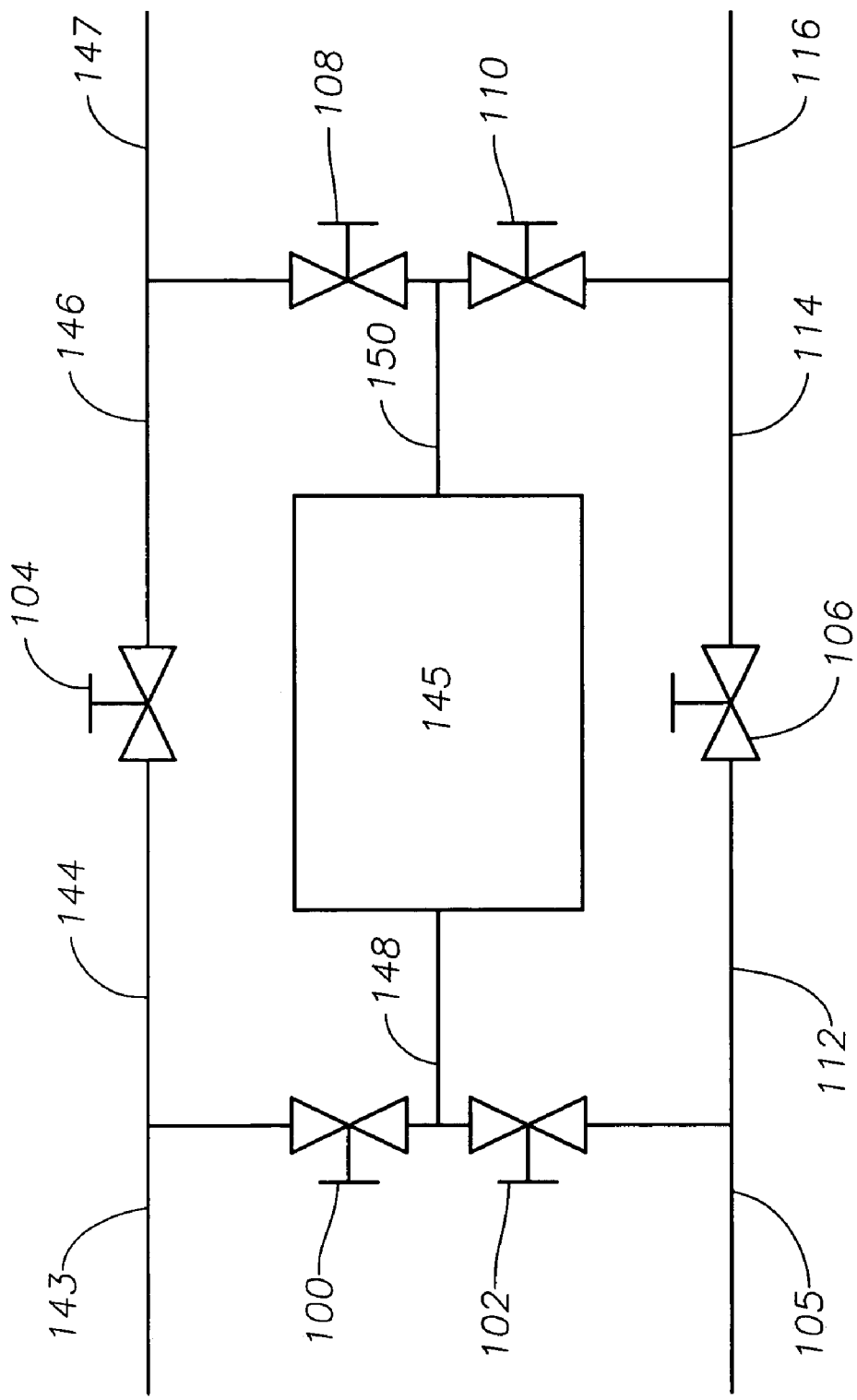

FIG. 2 illustrates a preferred embodiment of the switching means to switch the ion exchange bed 145 between a water treatment mode and a solvent treatment mode. Under the water treatment mode, valves 102 and 110 are close, valves 100, 106, and 108 are open, and valve 104 is closed or partially open. The combined water stream is directed via a line 143, passing through the valve 100 which is open, and is further directed to line 148 to the ion exchange bed 145 where substantially all contaminants such as acids or acid salts in the combined stream are removed by ion exchange. The exchanged stream now substantially free of contaminants, is further directed via a line 150 passing through valve 108 which is open, and is further directed via line 147 to downstream processes. A portion of the combined water stream can bypass the ion exchange bed 145 via a line 144, passing through valve 104 if the valve 104 is partially open, and is withdrawn via a line 146. Under the solvent treatment mode, valves 102, 104 and 110 are open, valves 100 and 108 are closed, and valve 106 is closed or partially open. The solvent is directed via line 105, passes through the valve 102 which is open, and is further directed to line 148 to the ion exchange bed 145 where substantially all contaminants such as acids or acid salts in the solvent, are removed by ion exchange. The exchanged stream now substantially free of contaminants, is further directed via line 150 passing through valve 110 which is open, and is further directed via line 116 to downstream processes. A portion of the solvent can bypass the anion exchanger bed 145 via line 112, passes through valve 106 if the valve 106 is partially open, and is withdrawn via a line 114.

The term "aromatic hydrocarbons", as used herein, shall mean hydrocarbons containing at least one aromatic ring comprising benzene, toluene, mono- and multi-alkyl benzenes, naphthalene, mono- and multi-alkyl naphthalenes, or mixture thereof.

The term "aliphatic hydrocarbons", as used herein, shall mean non-aromatic hydrocarbons with straight- or branched-chain arrangement or cyclic arrangement of the constituent carbon atoms. The aliphatic hydrocarbons comprise 1) paraffins; 2) olefins (alkenes, or alkadienes), which contain a least a double bond between carbon atoms; 3) acetylenes (alkynes), which contain at least a triple bond between carbon atoms; and 4) cyclo-paraffins, cycle-olefins, and cycle alkynes.

The term "solvent", used herein, shall mean a compound or a mixture of compounds which selectively dissolves aromatic hydrocarbons over aliphatic hydrocarbons. Examples such solvent in common commercial use include sulfolane, tetraethylene glycol, and n-formylmorpholine or a mixture of thereof. The solvent may also contain a substantial amount of other hydrocarbons (e.g., aromatics, paraffins, sulfone, coke, and acetone), water, organic and/or inorganic acids, salts, and other contaminants.

The term "water stream", used herein, shall mean a stream comprising essentially water. The water stream may also contain a substantial amount of solvent, salt, dissolved hydrocarbons, acids, and other contaminants.

This invention is applicable to processes in which mixtures of aromatic and aliphatic (including cycloaliphatic) hydrocarbons are separated by extraction of the aromatic hydrocarbons and stripping the aromatic hydrocarbons from the extracting solvent. The hydrocarbons can have from 4 to 12 carbon atoms and preferably have 6 to 8 carbon atoms in commercially more important embodiments.

The UOP Sulfolane™ process is a liquid-liquid extraction process to recover high-purity aromatics from hydrocarbon mixtures, such as reformate, pygas, or coke-oven light oil. This process is described in the *Handbook of Petroleum Refining Process,* 2nd edition (1996) p. 2.13, incorporated herein by reference as to that description.

The extracting solvent is any liquid that preferentially extracts aromatic hydrocarbons over aliphatic hydrocarbons. The boiling point of the extraction solvent should be higher than the boiling point of the aromatic hydrocarbons being extracted (i.e., it should have a boiling point of at least 100° C. and preferably between about 200° C. and about 300° C.) so that it is not evaporated during stripping. The preferred extracting solvent is sulfolane, available as sulfolane W™ from Phillips Chemical Company, Bartleavilla, Okla., USA.

The preferred ion exchange resin for solvent is macroreticular (i.e., has large pores) beads, however other resins, e.g., gel beads, also work in a diminished capacity. The preferred ion exchange resin for water is gel bead. Resin may be mixed acid/base or exclusively basic. Preferably a strong base anion exchange resin is used as those resins have higher operating capacities, which means that the resin may be regenerated/replaced less frequently. Examples of strong base resins include resins containing a quaternary ammonium group attached to a polymeric backbone with hydroxyl as the counter ion. The amine can readily adsorb acid anions (i.e. chloride) and release water. Examples of weak base resins include resins having tertiary amines as an active group. The tertiary amine function may be, for example, the N,N-dimethyl amine group or the N,N-diethyl amine group. The backbones of the resins can be polystyrene, divinylbenzene, acrylic, or other polymers; a styrene-divinylbenzene backbone is preferred as it is readily available and works well. Preferably, enough anion exchange resin is used to last for one to six months.

The anion exchange resin can be regenerated by contacting the anion exchange resin with a basic solution at an elevated temperature ranging from 25° C. to 200° C. Examples of the basic solution include NaOH, KOH, $NH_4OH$, LiOH, RbOH, CsOH, $Be(OH)_2$, $Mg(OH)_2$, $Ca(OH)_2$, $Sr(OH)_2$, and $Ba(OH)_2$ in aqueous or organic ionic solutions. Examples of organic ionic solution include methanol, ethanol, dimethylsulfone (DMSO), and aqueous solution or the above mentioned organic solvents. The cation exchange resin can be regenerated by contacting the cation exchange resin with an acidic solution at an elevated temperature ranging from 25° C. to 200° C. Examples of the acidic solution include HCl, $H_2SO_4$, $HNO_3$, acetic acid, oxalate acid, in aqueous or organic ionic solutions. Examples of organic ionic solution include methanol, ethanol, dimethylsulfone (DMSO), and aqueous solution or the above mentioned organic solvents.

The pH of the streams before and after resin bed treatment can be measured using any commercial available pH meters. Examples of available commercial pH meters include Corning™ Scholar 425 pH meter. The chloride concentration the streams before and after resin bed treatment can be measured using any commercial available chloride ion-selective-electrode (ISE) meters. Examples of the commercial available chloride ion-selective-electrode meters include ORION™ ion selective chloride meter, available from Sigma-Aldrich Corporation of Milwaukee, Wis., USA.

The following example further illustrates this invention.

EXAMPLE

The process of this invention was tested in the embodiment shown in FIG. 1. Ion exchange column 45 was packed with Rohm & Haas Amberlite® IRN78 strong base anion resin having a quaternary ammonium group attached to a styrene-divinyl benzene backbone. A full stream flow of 20.4 metric ton per hour of water in line 43 having an initial pH of about 5.5 to about 6 was treated. The test was run continuously for one month. The water product in line 47 had a pH of about 6 to 6.5 and no chloride detected over the entire one month test period. Following this one month test, the ion exchange column was removed from the process line and the water stream pH dropped to about 4.0 after 1 to 2 days of operation.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A process for separating hydrocarbons within a feed, comprising:
    A) extracting at least a majority of aromatic hydrocarbons with a sulfolane solvent from said feed to produce a first product and removing unextracted hydrocarbons as a second product;
    B) separating at least a portion of said aromatic hydrocarbons from said solvent in said first product with steam;
    C) condensing said steam to produce a first stream;
    D) processing at least a portion of said first stream through an ion exchange bed to produce a second stream; and
    E) washing said second product with said second stream of step (D).

2. The process recited in claim 1 wherein said ion exchange bed comprises a mixed cation/anion exchange resin.

3. The process recited in claim 1 wherein said ion exchange bed comprises a basic anion exchange resin.

4. The process recited in claim 3 wherein said basic anion exchange resin is a strong base resin.

5. The process recited in claim 3 wherein said basic anion exchange resin is loaded with hydroxyl ions.

6. The process recited in claim 3 wherein said basic anion exchange resin has tertiary amine active sites.

7. The process recited in claim 3 wherein said basic anion exchange resin has quaternary amine active sites.

8. The process recited in claim 1, further comprising:
    F) heating said washed stream to produce said steam in step (B).

9. The process recited in claim 1, further comprising providing a switching means to switch the feed to said ion exchange bed from said first stream to said solvent of step (B).

10. The process as set forth in claim 1 wherein said process is controlled to maintain the pH of said first stream in the range of 6 to 6.5.

11. A process for extracting aromatic hydrocarbons from a mixed hydrocarbon feed, comprising:
    A) extracting at least a majority of aromatic hydrocarbons with a solvent from said feed to produce a first product and removing unextracted hydrocarbons as a second product;

B) separating at least a portion of said aromatic hydrocarbons from said solvent in said first product with steam;
C) condensing said steam to produce a first stream;
D) processing at least a portion of said first stream through an ion exchange bed to produce a second stream;
E) providing a switching means to switch feed to said ion exchange bed from said first stream to said solvent, such that said solvent can be passed through said ion exchange bed following step (B); and
F) processing at least a portion of said solvent through an ion exchange bed to produce a processed solvent.

12. The process recited in claim 11 wherein said ion exchange bed comprises a mixed cation/anion exchange resin.

13. The process recited in claim 11 wherein said ion exchange bed comprises a basic anion exchange resin.

14. The process recited in claim 13 wherein said basic anion exchange resin is a strong base resin.

15. The process recited in claim 13 wherein said basic anion exchange resin is loaded with hydroxyl ions.

16. The process recited in claim 13 wherein said basic anion exchange resin has tertiary amine active sites.

17. The process recited in claim 13 wherein said basic anion exchange resin has quaternary amine active sites.

18. The process recited in claim 11, further comprising washing said second product with said second stream of step (D).

19. The process recited in claim 11, further comprising:
G) washing said second product with said second stream of step (D); and
H) heating said washed second stream to produce said steam in step (B).

20. The process recited in claim 11, wherein said solvent is sulfolane.

21. The process recited in claim 11, further comprising recycling said processed solvent to step (A).

22. A process for removing acids in a system for processing a feed including $C_4$ to $C_{12}$ hydrocarbons; said process comprising:
A) extracting at least a majority of aromatic hydrocarbons with a sulfolane solvent from said feed to produce a first product and removing unextracted hydrocarbons in said feed as a second product;
B) separating at least a portion of said aromatic hydrocarbons from said solvent in said first product with steam;
C) condensing said steam to produce a first stream;
D) washing said second product with said first stream;
E) processing at least a portion of said first stream through an ion exchange bed to produce a second stream; and
F) providing a switching means to switch feed to said ion exchange bed from said first stream to said solvent of step (B).

23. The process recited in claim 22 wherein said ion exchange bed comprises mixed cation/anion exchange resin.

24. The process recited in claim 22 wherein said ion exchange bed comprises a basic anion exchange resin.

25. The process recited in claim 24 wherein said basic anion exchange resin is a strong base resin.

26. The process recited in claim 24 wherein said basic anion exchange resin is loaded with hydroxyl ions.

27. The process recited in claim 24 wherein said basic anion exchange resin has tertiary amine active sites.

28. The process recited in claim 24 wherein said basic anion exchange resin has quaternary amine active sites.

29. The process recited in claim 22 wherein said acids comprises hydrochloride acid.

30. The process recited in claim 22 further comprises heating said second stream to produce said steam in step (B).

31. A process for removing acids in a system for processing a feed including $C_4$ to $C_{12}$ aliphatic and aromatic hydrocarbons; comprising:
A) extracting at least a majority of aromatic hydrocarbons with a sulfolane solvent, said solvent comprising sulfolane, from said feed to produce a first product and removing unextracted hydrocarbons in said feed as a second product;
B) separating said first product into an overhead product and a bottom product, condensing said overhead product to produce a condensed overhead hydrocarbon stream and a condensed overhead aqueous stream;
C) separating at least a portion of said aromatic hydrocarbons from said solvent in said first product with steam;
D) condensing said steam to produce a first stream;
E) washing said second product with said first stream;
F) combining said first stream in step (E) and said condensed overhead aqueous stream in step (B);
G) processing at least a portion of said combined stream through an ion exchange bed to produce a second stream; and
H) heating said second stream to produce said steam in step (C).

32. The process recited in claim 31 wherein said ion exchange bed comprises a mixed cation/anion exchange resin.

33. The process recited in claim 31 wherein said ion exchange bed comprises a basic anion exchange resin.

34. The process recited in claim 33 wherein said basic anion exchange resin is a strong base resin.

35. The process recited in claim 33 wherein said basic anion exchange resin is loaded with hydroxyl ions.

36. The process recited in claim 33 wherein said basic anion exchange resin has tertiary amine active sites.

37. The process recited in claim 33 wherein said basic anion exchange resin has quaternary amine active sites.

38. The process recited in claim 31, further comprising a switching means to switch feed to said ion exchange bed from said first stream to said solvent of step (C).

39. The process recited in claim 31 wherein the first product is at least one kilogram per hour.

* * * * *